(12) United States Patent
Noy et al.

(10) Patent No.: US 7,569,850 B2
(45) Date of Patent: Aug. 4, 2009

(54) LIPID BILAYERS ON NANO-TEMPLATES

(75) Inventors: Aleksandr Noy, Belmont, CA (US); Alexander B. Artyukhin, Menlo Park, CA (US); Olgica Bakajin, San Leandro, CA (US); Pieter Stoeve, Davis, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 178 days.

(21) Appl. No.: 11/338,513

(22) Filed: Jan. 23, 2006

(65) Prior Publication Data

US 2006/0169975 A1 Aug. 3, 2006

Related U.S. Application Data

(60) Provisional application No. 60/646,905, filed on Jan. 24, 2005.

(51) Int. Cl.
*H01L 35/24* (2006.01)
*H01L 51/00* (2006.01)

(52) U.S. Cl. .................. 257/40; 257/213; 424/450; 438/1; 977/702; 977/907; 530/326

(58) Field of Classification Search .............. 257/40, 257/213; 977/702, 902; 424/450; 438/1; 530/326
See application file for complete search history.

(56) References Cited

U.S. PATENT DOCUMENTS

| 5,368,712 A * | 11/1994 | Tomich et al. ......... 204/403.06 |
|---|---|---|
| 6,203,864 B1 | 3/2001 | Zhang et al. |
| 6,325,909 B1 | 12/2001 | Li et al. |
| 6,515,325 B1 | 2/2003 | Farnworth et al. |
| 6,913,697 B2 | 7/2005 | Lopez et al. |
| 6,977,155 B2 | 12/2005 | Lahiri et al. |
| 2002/0027312 A1 | 3/2002 | Yakobson |
| 2003/0044608 A1 | 3/2003 | Yoshizawa et al. |
| 2003/0134433 A1* | 7/2003 | Gabriel et al. .............. 436/518 |
| 2004/0023372 A1* | 2/2004 | Klein et al. .............. 435/317.1 |
| 2004/0142172 A1* | 7/2004 | Sugiyama et al. ........... 428/403 |
| 2004/0253741 A1 | 12/2004 | Star et al. |
| 2005/0037374 A1 | 2/2005 | Melker et al. |
| 2005/0051805 A1 | 3/2005 | Kim et al. |
| 2005/0181409 A1 | 8/2005 | Park et al. |
| 2005/0260685 A1 | 11/2005 | Fang et al. |
| 2006/0054936 A1* | 3/2006 | Lieber et al. ................. 257/210 |

FOREIGN PATENT DOCUMENTS

WO WO 2004/031721 A2 4/2004

OTHER PUBLICATIONS

Artyukhin et al. (Journal of the American Chemical Society, 2005, 127, 7538-7542).*
Katz, E., et al., "Biomolecule-functionalized Carbon Nanotubes: Applications in Nanobioelectronics," ChemPhysChem 2004, 5, pp. 1084-1104.

* cited by examiner

*Primary Examiner*—Thanh V Pham
*Assistant Examiner*—Jami M Valentine
(74) *Attorney, Agent, or Firm*—Eddie E. Scott (57) ABSTRACT

A lipid bilayer on a nano-template comprising a nanotube or nanowire and a lipid bilayer around the nanotube or nanowire. One embodiment provides a method of fabricating a lipid bilayer on a nano-template comprising the steps of providing a nanotube or nanowire and forming a lipid bilayer around the polymer cushion. One embodiment provides a protein pore in the lipid bilayer. In one embodiment the protein pore is sensitive to specific agents.

23 Claims, 5 Drawing Sheets

LIPID BILAYERS ON NANO-TEMPLATES

CROSS-REFERENCE TO RELATED APPLICATIONS

This application claims the benefit of U.S. Provisional Patent Application No. 60/646,905 filed Jan. 24, 2005 by Aleksandr Noy, Alexander B. Artyukhin, Olgica Bakajin, and Pieter Stroeve and titled "One-dimensional Lipid Bilayers on Carbon Nanotube Templates." U.S. Provisional Patent Application No. 60/646,905 filed Jan. 24, 2005 and titled "One-dimensional Lipid Bilayers on Carbon Nanotube Templates" is incorporated herein by this reference.

The United States Government has rights in this invention pursuant to Contract No. W-7405-ENG-48 between the United States Department of Energy and the University of California for the operation of Lawrence Livermore National Laboratory.

BACKGROUND

1. Field of Endeavor

The present invention relates to nanotechnology and more particularly to lipid bilayers on nano-templates.

2. State of Technology

The article "Biomolecule-Functionalized Carbon Nanotubes: Applications in Nanobioelectronics" by Eugenii Katz and Itamar Willner in the August 2004 issue of *ChemPhysChem*, Vol. 5, Issue 8, pages 1085-1104 provides the following state of technology information, "The integration of biomaterials with CNTs enables the use of the hybrid systems as active field-effect transistors or biosensor devices (enzyme electrodes, immunosensors, or DNA sensors). Also, the integration of CNTs with biomolecules has allowed the generation of complex nanostructures and nanocircuitry of controlled properties and functions."

United States Patent Application No. 2005/0051805 by Byong Man Kim, et al for microprocessors with improved power efficiency published Mar. 10, 2005 provides the following state of technology information: "Nanotubes comprise nanometer scale tubular structures, typically made from a sheet of carbon atoms known as a graphene. They may be single wall or multi-wall structures. A single-walled carbon nanotube typically comprises an elongated, single hollow tube that is about 1 nm in diameter and few-hundreds-nm to few-hundreds-μm in length. A multi-walled carbon nanotube consists of a plurality of generally concentric, hollow tubes of different diameters that can range up to a few hundreds of nanometers. One popular method of synthesizing high quality carbon-nanotube structures uses a chemical vapour deposition technique based on a vapour-solid interaction of methane and hydrogen with a catalyst in a heated environment, as described by J. Kong, H. T. Soh, A. Cassell, C. F. Quate, H. Dai, Nature, 395, 878 (1998). A carbon-nanotube structure can act as a semiconductor or a metal, depending on its diameter and how it is rolled up from a sheet of graphene, and has been demonstrated to be harder than the steel and a better conductor than copper. Reference is directed to P. McEuen, M. Fuhrer, H. Park, IEEE Transactions on Nanotechnology, 1, 78 (2002). Various devices have been formed from carbon-nanotube structures. Ballistic conduction in nanotube structures has been reported where nanotubes placed between ferromagnetic contacts were used to demonstrate coherent transport of electron spin, as described by K. Tsukagoshi, B. Alphenaar and H. Ago, Nature, 401, 572 (1999). There have been a number of reports on the use of nanotube structures as the channel material of transistors which performed better than state of the art CMOS or SOI prototypes and reference is directed to S. Tans, A. Verschueren, and C. Dekker, Nature, 393, 49 (1998); R. Martel et al., Appl. Phys. Lett., 73, 2447 (1998); and A. Javey et al., Nature Materials, published online: 17 Nov. 2002; doi:10. 1038/nmat769. Logic functions have also been demonstrated from assembly of nanotube transistors, as described in V. Derycke, Nano Letters, 1, 453 (2001) and A. Bachtold et al., Science, 294, 1317 (2001). A single electron memory was demonstrated in which a nanotube channel of a transistor was used as a single electron sensor and manipulator—see M. Fuhrer et al., Nano Letters, 2, 755 (2002). Also, a nanotube channel of a transistor has been used as an IR source, in which the IR emission was achieved by recombining electrons and holes in the nanotube channel, injected from the source and drain of the transistor, as reported by J. A. Misewich et al., Science 300, 783 (2003). The structures described so far are demonstration devices and not apt to yield consistent device characteristics. Various methods of forming heterojunctions in carbon-nanotube structures have been proposed in an attempt to produce more reliable devices. Heterojunctions formed by adjoining carbon-nanotubes of differently rolled-up layers of closely packed carbon atoms of different diameters have been proposed in U.S. Pat. No. 6,538,262 to V. Crespi et al. Structures utilizing mechanical deformation i.e., by straining or bending are described in U.S. patent application Ser. No. 20020027312 A1, Mar. 7, 2002. Chemical doping of carbon-nanotube structures has been proposed by C. Zhou, Science, 290, 1552 (2000) to B. Yakobson. Also, a method of forming a heterojunction in a nanotube structure by means of a heat induced solid-solid diffusion and chemical reaction is described in U.S. Pat. No. 6,203,864 to Y. Zhang and S. Iijima. However, these junction forming techniques are not particularly suited to forming transistor structures. U.S. patent application Ser. No. 20030044608 A1 by H. Yoshizawa discloses a number of nanotube structures in which an outer graphene sheet is chemically modified to change its conductive characteristics, but the resulting structure does not exhibit a transistor action. It has been proposed to use Y-shaped nanotube structures to form transistors as described in U.S. Pat. No. 6,325,909 to J. Li et al. The transistor action results from heterojunctions formed by structural defects in the vicinity of the confluence of the arms of the Y-shaped nanotube and so the device lacks reproducibility. Also, transistors comprising vertically extending nanotube structures have been proposed in U.S. Pat. No. 6,515,325 to W. Farnworth, and U.S. Pat. No. 6,566,704 to W. Choi et al. However, vertical nanotube structures are known to include a high density of various defects and exhibit poor semiconductor properties, degrading performance of the transistor."

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention provides a lipid bilayer on a nano-template comprising a nanotube or nanowire and a lipid bilayer around the nanotube or nanowire. One embodiment provides a method of fabricating a lipid bilayer on a nano-template comprising the steps of providing a nanotube or nanowire and forming a lipid bilayer around the polymer cushion. One embodiment provides a protein pore in the lipid bilayer. In one embodiment the protein pore is sensitive to specific agents.

The present invention provides a lipid bilayer structure that integrates nanotubes or nanowires with a key biological environment—phospholipid membrane. The structure of one embodiment of the present invention provides lipid bilayers wrapped around carbon nanotubes or nanowires modified with a hydrophilic polymer cushion layer. Despite high bilayer curvature, the lipid membrane maintains its fluidity and can sustain repeated damage-recovery cycles. The present invention provides a system of spontaneous insertion of pore-forming proteins into the lipid bilayer.

One embodiment of the present invention provides a lipid bilayer on a nanotube or nanowire template comprising a nanotube or nanowire, a lipid bilayer around the nanotube or nanowire, and a polymer cushion between the nanotube or nanowire and the lipid bilayer. Another embodiment of the present invention provides a lipid bilayer on a nanotube or nanowire template and a protein pore in the lipid bilayer. Another embodiment of the present invention provides a method of fabricating a lipid bilayer on a nanotube or nanowire template comprising the steps of providing a nanotube or nanowire, coating the nanotube or nanowire with at least one layer of polymer cushion, and forming a lipid bilayer around the polymer cushion. Another embodiment of the present invention includes a step of incorporating a protein pore in the lipid bilayer.

The present invention is expected to provide new classes of biosensors and bioelectronic devices. Uses of the present invention include novel biosensor construction, fabrication of novel bio-inorganic materials, new techniques for live cell probing using the coated nanotubes or nanowires as nanoelectrodes, and other uses.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF THE INVENTION

Referring to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

Carbon nanotubes and nanowires have catalyzed many important discoveries in physics, chemistry and materials science. To achieve a similar success with biophysical applications, such as biosensing, intracellular probing, and bio-NEMS, the challenge of integrating nanotubes or nanowires with key biological environments must be met. Many vital biological proteins function only in a bilayer membrane environment. The present invention provides a new way of functionalizing a single wall carbon nanotube or nanowire surface with a phospholipid bilayer, which is a main component of biological membranes. In one embodiment, the nanotube or nanowire surface, modified with hydrophilic polymer layers, serves as a template for assembly of the lipid bilayer, which forms a continuous shell around the nanotube or nanowire. The supported bilayers maintain the key properties of biological membranes: the lateral mobility of lipid molecules and the ability to incorporate membrane proteins. The present invention provides a robust and general strategy for achieving biocompatibility of carbon nanotubes and nanowires.

Figure 1:
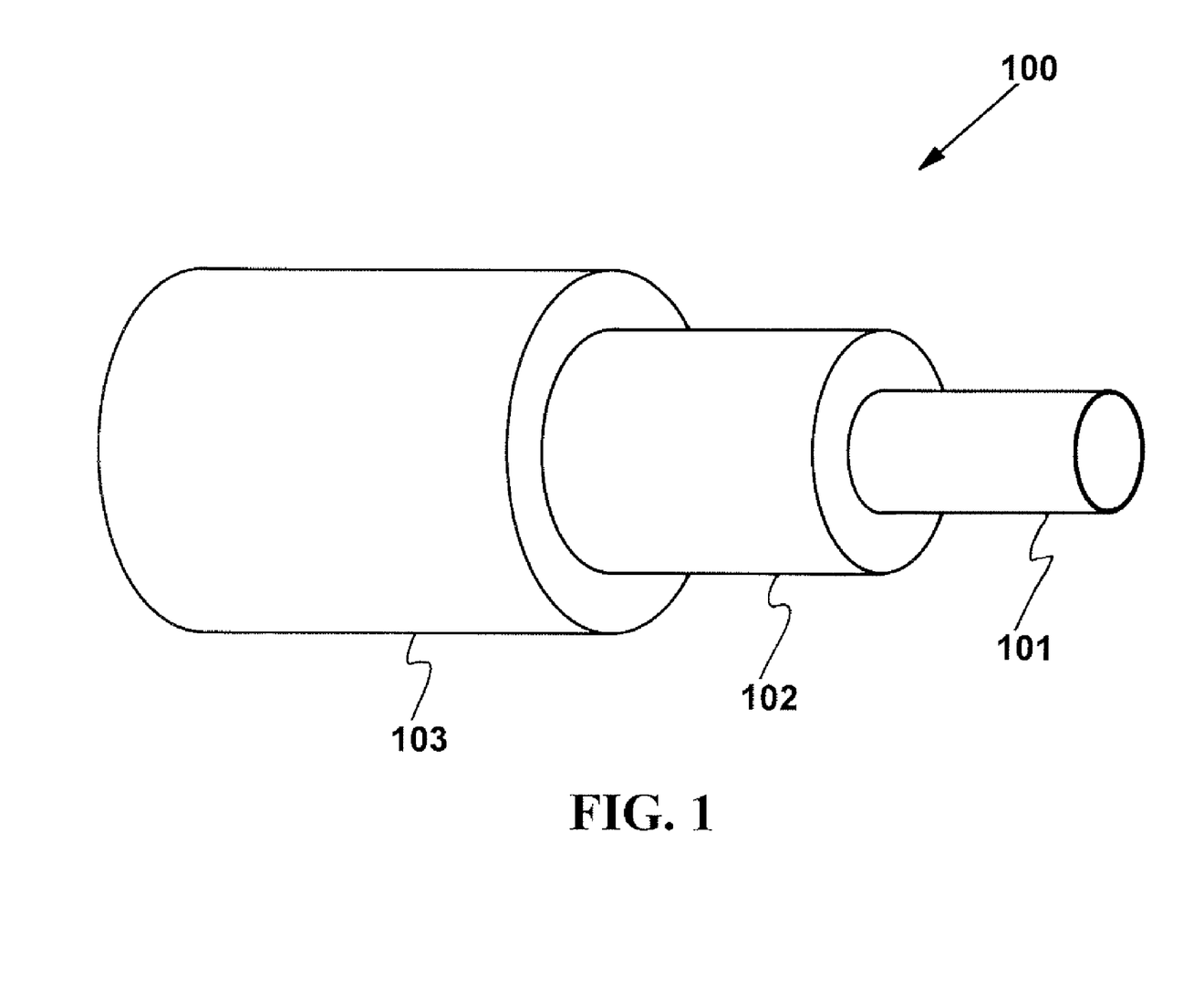
FIG. 1 illustrates one embodiment of a one-dimensional lipid bilayer on a nano-template constructed in accordance with the present invention.

Referring now to FIG. 1, one embodiment of a lipid bilayer on a nano-template constructed in accordance with the present invention is illustrated. The lipid bilayer on a nano-template is designated generally by the reference numeral 100. The lipid bilayer on a nano-template 100 can be briefly described as a nanotube or nanowire 101 encapsulated by a lipid bilayer 103 resting on a polymer "cushion" layer 102.

The specific lipid bilayer on a nano-template 100 shown in FIG. 1 is a one-dimensional (1-D) lipid bilayer structure that integrates a carbon nanotube 101 with a key biological environment—phospholipid membrane 103. The lipid bilayer on a nano-template 100 provides a lipid bilayer 103 wrapped around the carbon nanotube 101 modified with a hydrophilic polymer cushion layer 102. It is to be understood that other embodiments include other forms of nano-templates 101, lipid bilayers 103, and polymer cushions 102. For example, the nano-template can be a nanowire 101, the lipid bilayer can be a one-dimensional (1-D) lipid bilayer 102, and the polymer cushion can be a hydrophilic polymer cushion layer 102.

Despite high bilayer curvature, the lipid membrane maintains its fluidity and can sustain repeated damage-recovery cycles. The present invention provides a system of spontaneous insertion of pore-forming proteins into 1-D lipid bilayers. The one-dimensional lipid bilayer on a carbon nanotube template 100 provides a new class of biosensor and bioelectronic device. Uses of the one-dimensional lipid bilayer on a carbon nanotube template 100 include novel biosensor construction, fabrication of novel bio-inorganic materials, new techniques for live cell probing using the coated nanotubes as nanoelectrodes, and other uses.

Figure 2:
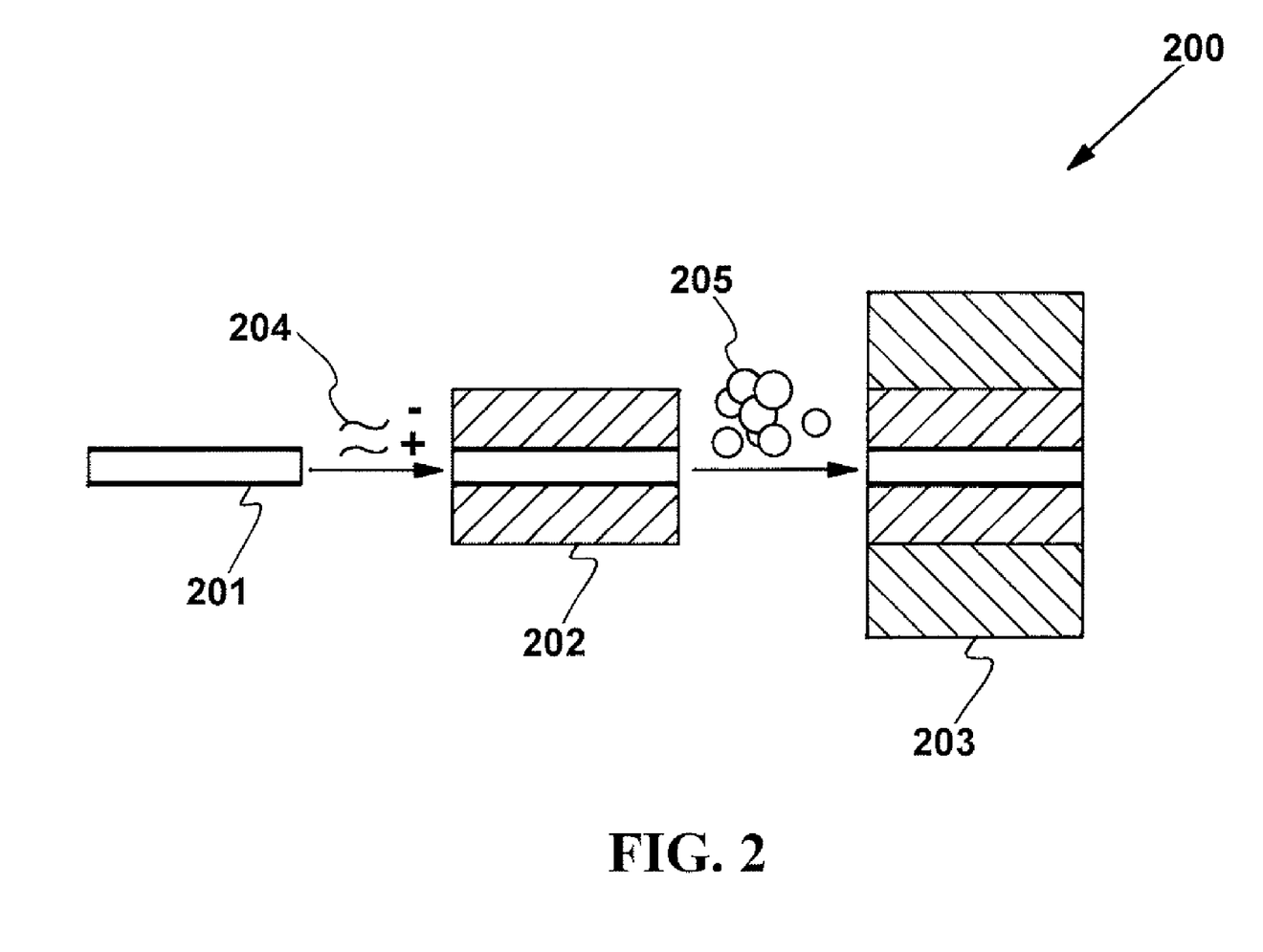
FIG. 2 is a schematic of a system of fabricating a polymer and a lipid assembly on a nanotube or nanowire.

Referring now to FIG. 2, the fabrication of the lipid bilayer on a nano-template will now be described. The system of fabrication of the lipid bilayer on a nano-template is designated generally by the reference numeral 200. It is to be understood that other embodiments include various forms of nano-templates, lipid bilayers, and polymer cushions 102.

FIG. 2 provides a schematic of a polymer and lipid assembly on a carbon nanotube or nanowire. FIG. 2 will be described with reference to a nanotube; however, it is to be understood that a nanowire could be used instead of the nanotube.

First, a carbon nanotube 201 is coated with several alternating layers 202 of oppositely charged polyelectrolytes, followed by the formation of lipid bilayer 203 by vesicle fusion. The opposite charges are illustrated at 204.

Single-wall nanotubes 201 are grown on TEM grids using catalytic CVD synthesis to produce suspended carbon nanotubes suitable for modification process. A polymer coating 202 is formed on these suspended carbon nanotubes 201 by exposing them to the alternating solutions of polyanions and polycations.

Formation of a lipid bilayer around a naked carbon nanotube presents challenges. First, typical diameters of single-wall carbon nanotubes range from 1-2 nm, which is below a critical curvature of a common phospholipids bilayer. Second, the hydrophobic nanotube surface promotes the formation of a monolayer, not the bilayer that is necessary for membrane channel support. To remedy these problems Applicants placed a semi-permeable hydrophilic polymer "cushion" layer between the nanotube and the bilayer. This layer is important for a number of reasons. First, the polymer provides hydrophilic support surface for the bilayer. Second, the additional polymer layer between the nanotube and the bilayer increases the size of the structure and helps to match the size of the support to the critical bilayer curvature. Third, interactions of the lipid headgroups with the polymer "cushion" stabilize the bilayer and increase its robustness. Fourth, the polymer "cushion," which typically contains up to 50% water, lifts the membrane from the substrate and helps to maintain natural environment for inserted protein channels, which may protrude past the bilayer.

The 1-D Bilayer 203 formation is started by creating supported lipid bilayers 203 on the "cushioned" carbon nanotubes 201 using vesicle fusion 205. The multilayer polymer cushion 202 on nanotubes 203 with a cationic layer (PDDA or PAH) to stabilize the bilayer that contains 75% of the anionic lipid (SOPS). To enable visualization of the final structure, the vesicles incorporated a small fraction of a fluorescent lipid probe (BODIPY-PC). Scanning confocal microscope images of the resulting structures show linear fluorescent features inside the holes of the TEM grid, which correspond to the lipidcoated carbon nanotubes stretching across the grid holes. These results indicate that partial strain relief in the dimension of the nanotube axis coupled with the electrostatic attraction of the bilayer to the polymer support is sufficient to stabilize the bilayer in 1-D configuration. Incorporation of charged lipids in the membrane should reject subsequent lipid multilayer formation. One important feature of a functional lipid bilayer 202 is the ability of the lipid molecules to diffuse along the bilayer plane.

The assembly process is started by modifying pristine suspended single-wall carbon nanotubes 101 with five alternating polymer layers 202 composed of strong polyelectrolytes, such as poly(diallyldimethylammonium chloride) (PDDA), sodium poly(styrenesulphonate) (PSS), and poly(allylamine hydrochloride) (PAH. critical (i.e., smallest) inner radius of the lipid bilayer is ca. 5 nm. Polyelectrolytes that form the cushion 202 produce 1 nm thick layers at low ionic strength conditions; therefore, five polymer layers were used to match the critical curvature of the bilayer 203.

TEM images show that five alternating PAH/PSS layers 202 produce smooth coating on the nanotubes 201 over large distances, with the diameter of the final structure of 10-15 nm. Substitution of PAH to PDDA produces rougher coating of 10-30 nm in diameter. Overall, the addition of the polymer cushion 202 made the size of the nanotubes 201 comparable (and in some cases even larger) to the smallest reported nanoparticles (14 nm) that can support lipid bilayers.

Applicants used bare TEM grids as a substrate to grow suspended carbon nanotubes 201. The fabrication begins with assembly of common phospholipids into tubular one-dimensional geometry by using the carbon nanotube 201 as assembly template. The nanotube surface is modified with a hydrophilic polymer layer 202 and then a continuous lipid bilayer shell 203 is assembled around this structure. Applicants used ultrasonication to prepare lipid vesicles composed of 1-stearoyl-2-oleoyl-sn-glycero-3-[phospho-Lserine]sodium salt (SOPS), 1-palmitoyl-2-oleoyl-sn-glycero-3-phosphocholine (POPC), and 2-(4,4-difluoro-5-methyl-4-bora-3a,4a-diazas-indacene-3-do-decanoyl)-1-hexadecanoyl-sn-glycero-3-phosphocholine (BODIPY-PC) in the ratio 75:23:2. The grid with polymercoated carbon nanotubes was incubated with vesicles for 40-50 min.

The lipid membrane maintains its fluidity in 1-D geometry, and the mobility of lipid molecules can still be described by a simple diffusion model. The one-dimensional lipid bilayer on a carbon nanotube template is highly robust and can sustain repeated damage-recovery cycles. These properties enable development of a range of functional bioinorganic nanostructures based on 1-D lipid bilayers.

Referring now to FIG. 3, a one-dimensional lipid bilayer on a carbon nanotube template with an oligomeric protein pore constructed in accordance with the present invention is illustrated. The one-dimensional lipid bilayer on a carbon nanotube template with an oligomeric protein pore is designated generally by the reference numeral 300. The one-dimensional lipid bilayer on a carbon nanotube template with an oligomeric protein pore 300 can be briefly described as a carbon nanotube 301 encapsulated by a lipid bilayer 303 resting on a polymer "cushion" layer 302 with an oligomeric protein pore 304.

The one-dimensional lipid bilayer on a carbon nanotube template 300 is a one-dimensional (1-D) lipid bilayer structure that integrates carbon nanotubes with a key biological environment—phospholipid membrane. The one-dimensional lipid bilayer on a carbon nanotube template 300 provides lipid bilayers 303 wrapped around carbon nanotubes 301 modified with a hydrophilic polymer cushion layer 302 and with an oligomeric protein pore 304. Despite high bilayer curvature, the lipid membrane maintains its fluidity and can sustain repeated damage-recovery cycles.

Referring now to FIG. 4, the fabrication of a one-dimensional lipid bilayer on a carbon nanotube template with an oligomeric protein pore will now be described. The system of fabrication of a one-dimensional lipid bilayer on a carbon nanotube template with an oligomeric protein pore is designated generally by the reference numeral 400.

First, carbon nanotubes 401 are coated with alternating layers of oppositely charged polyelectrolytes 402, followed by the formation of lipid bilayer 403 by vesicle fusion. Additional exposure to the solution of an agent is used to form the protein pore 404. In the illustration of FIG. 4, a monomeric bacterial toxin (PA63 fragment of the anthrax toxin 405 shown) results in the formation of the oligomeric protein pore 404 in the bilayer membrane. It is to be understood that other agents than the anthrax toxin 405 can be used. The agents can be biowarfare agents or health related agents. For example, the agents can include a full spectrum of biowarfare agents including bacteria, viruses and toxins, examples of which include Anthrax, Smallpox, Plague, Botulism, Tularemia, and Viral hemorrhagic fever. The agents can also include a full spectrum of health related agents including bacteria, viruses and toxins, examples of which include SARS and avian flu. A list of some of the agents is provided below in Table 1.

TABLE 1

List of Agents

Figure 3:
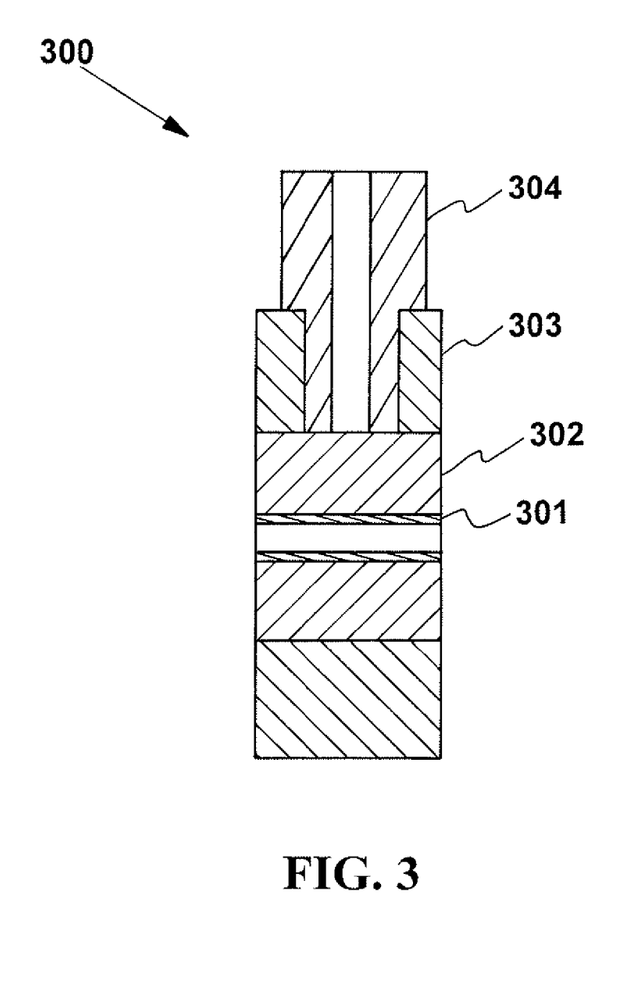
FIG. 3 illustrates a lipid bilayer on a nanotemplate with a protein pore constructed in accordance with the present invention.
Figure 4:
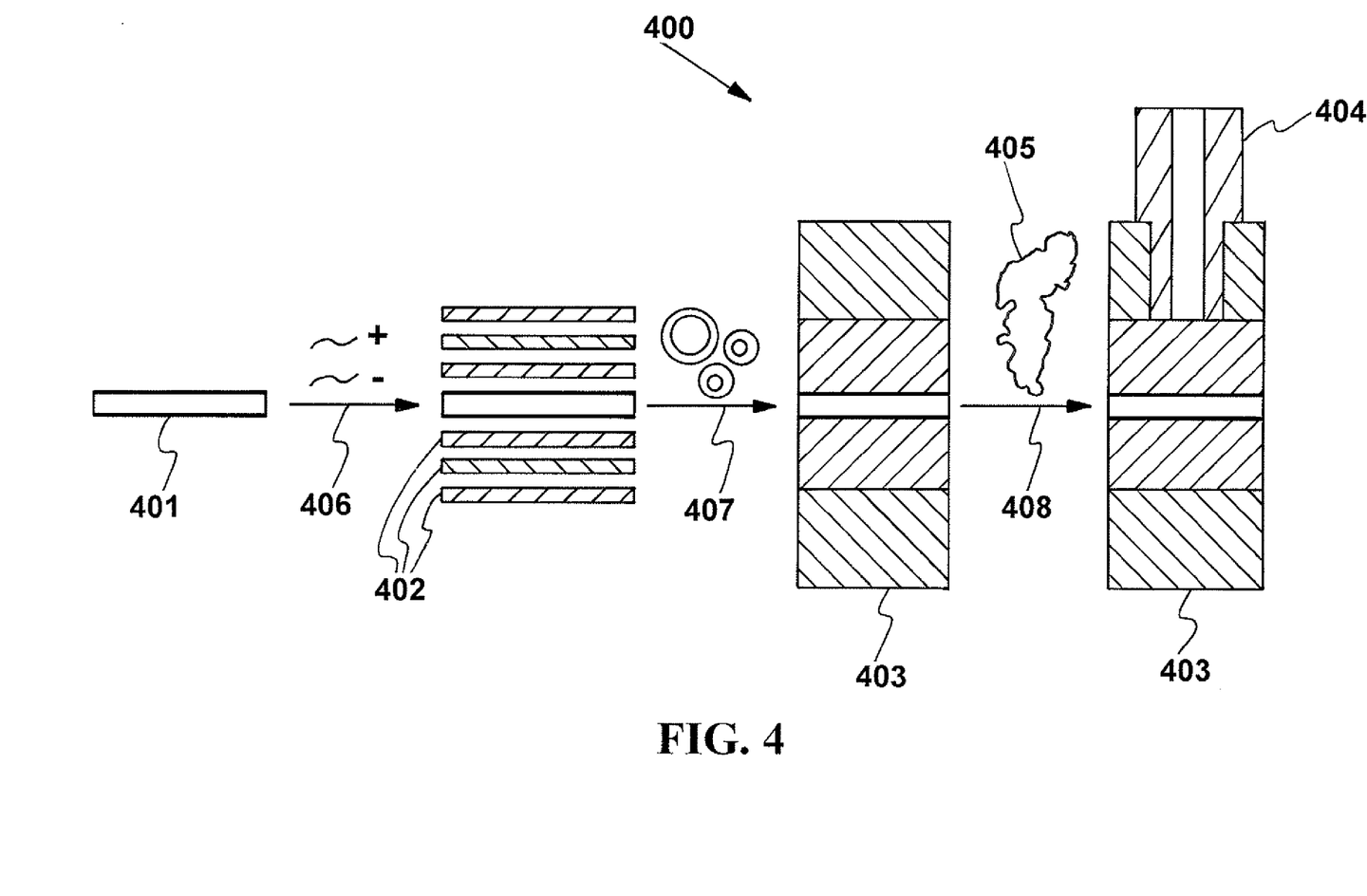
FIG. 4 is a schematic of a system of fabricating a lipid bilayer on a nanotemplate with a protein pore.

Abrin
Acids (caustics)
Adamsite (DM)
Americium-241 (Am-241)
Ammonia
Anthrax (*Bacillus anthracis*)
Arenaviruses
Arsenic
Arsine (SA)
Avian flu
*Bacillus anthracis* (anthrax)
Barium
Benzene
Bioterrorism agents
Biotoxins
Blister agents/vesicants
Blood agents
Botulism
Brevetoxin
Bromine (CA)
Bromobenzylcyanide (CA)
*Brucella* species (brucellosis)
Brucellosis (*Brucella* species)
*Burkholderia mallei* (glanders)
*Burkholderia pseudomallei*
BZ
Carbon Monoxide
Caustics (acids)
Cesium-137 (Cs-137)
Chemical agents
*Chlamydia psittaci* (psittacosis)
Chlorine (CL)
Chloroacetophenone (CN)
Chlorobenzylidenemalononitrile (CS)
Chloropicrin (PS)
Choking/lung/pulmorary agents
Cholera (*Vibrio cholerae*)
*Clostridium botulinum* toxin
*Clostridium perfringens*
Cobalt-60 (Co-60)
Colchicine New March 15
*Coxiella burnetii* (Q fever)
Cyanide
Cyanogen chloride (CK)
Dibenzoxazepine (CR)
Digitalis New March 16
Diphosgene (DP)
Distilled mustard (HD)
Ebola virus hemorrhagic fever
*E. coli* O157:H7 (*Escherichia coli*)
Nipah virus & hantavirus
Epsilon toxin of *Clostridium perfringens*
*Escherichia coli* O157:H7 (*E. coli*)
Ethylene glycol
Fentanyls & other opioids
*Francisella tularensis* (tularemia)
Glanders (*Burkholderia mallei*)
Hydrofluoric acid (hydrogen fluoride)
Hydrogen chloride
Hydrogen cyanide (AC)
Hydrogen fluoride
Incapacitating agents
Iodine-131 (I-131)
Lassa fever
Lewisite (L, L-1, L-2, L-3)
Long-acting anticoagulant
Lung/choking/pulmonary agents
Marburg virus hemorrhagic fever
Melioidosis
Methyl Bromide
Methyl Isocyanate
Mudslides & landslides TABLE 1-continued List of Agents Mustard gas (H) (sulfur mustard)
Mustard/lewisite (HL)
Mustard/T
Nerve agents
Nitrogen mustard (HN-1, HN-2, HN-3)
Opioids
Osmium tetroxide
Paraquat
Phosgene (CG)
Phosgene oxime (CX)
Phosphine
Phosphorus, elemental, white or yellow
Plague (*Yersinia pestis*)
Plutonium-239 (Pu-239)
Potassium cyanide (KCN)
Psittacosis (*Chlamydia psittaci*)
Pulmonary/choking/lung agents
Q fever (*Coxiella burnetii*)
Radioisotopes (radioactive isotopes)
Radioactive isotopes (radioisotopes)
Ricin toxin from *Ricinus communis*
*Rickettsia prowazekii* (typhus fever)
*Salmonella* species (salmonellosis)
*Salmonella* typhi (typhoid fever)
Salmonellosis (*Salmonella* species)
Sarin (GB)
SARS
Saxitoxin
Sesqui mustard
*Shigella* (shigellosis)
Shigellosis (*Shigella*)
Smallpox (*variola major*)
Sodium azide
Sodium cyanide (NaCN)
Sodium Monofluoroacetate
Soman (GD)
Staphylococcal enterotoxin B
Stibine
Strontium-90 (Sr-90)
Strychnine
Sulfuryl Fluoride
Sulfur mustard (H) (mustard gas)
Super warfarin
Tabun (GA)
Tetrodotoxin
Thallium
Trichothecene New March 17
Tularemia (*Francisella tularensis*)
Typhoid fever (*Salmonella typhi*)
Typhus fever (*Rickettsia prowazekii*)
Uranium-235 (U-235)
Uranium-238 (U-238)
*Variola major* (smallpox)
Vesicants/blister agents
*Vibrio cholerae* (cholera)
Viral encephalitis
Viral hemorrhagic fevers
Vomiting agents
VX one-dimensional lipid bilayer on a carbon nanotube template 300 provides a new class of biosensor and bioelectronic device. Uses of the one-dimensional lipid bilayer on a carbon nanotube template 300 include novel biosensor construction, fabrication of novel bio-inorganic materials, new techniques for live cell probing using the coated nanotubes as nanoelectrodes, and other uses.

One use of the present invention is in novel biosensor construction. The novel biosensor construction is described in co-pending U.S. patent application Ser. No. 11/338,512 for a Lipid Nanotube or Nanowire Sensor filed Jan. 23, 2006 by Aleksandr Noy, Olgica Bakajin, Sonia Létant, Michael Stadermann, and Alexander B. Artyukhin. U.S. patent application Ser. No. 11/338,512 for a Lipid Nanotube or Nanowire Sensor filed Jan. 23, 2006 by Aleksandr Noy, Olgica Bakajin, Sonia Létant, Michael Stadermann, and Alexander B. Artyukhin is incorporated herein by this reference.

As described in the co-pending United States Patent Application, a microfluidic device system incorporates a novel biosensor. Microfluidics is a multidisciplinary field comprising physics, chemistry, engineering and biotechnology that studies the behavior of fluids at the microscale and mesoscale, that is, fluids at volumes thousands of times smaller than a common droplet. It is a new science, having emerged only in the 1990s, so the number of applications for this technology is currently small. However, it is potentially significant in a wide range of technologies. Microfluidics is used in the development of DNA microarray technology, micro-thermal and micro-propulsion technologies, and lab-on-a-chip technology. Microfluidics also concerns the design of systems in which such small volumes of fluids will be used. The behavior of fluids at the microscale can differ from 'macrofluidic' behavior in that factors such as surface tension, energy dissipation, and electrokinetics start to dominate the system. Microfluidics studies how these behaviors change, and how they can be worked around, or exploited for new uses. A microfluidic device can be identified by the fact that it has one or more channels with at least one dimension less than 1 mm.

Nanowires and nanotubes provide a critical enabling technology for chem./bio sensing. Their surface-to-volume ratio is phenomenally high, therefore surface events such as binding of a protein or an ion can trigger a significant change in bulk electronic properties and enable electrical detection of binding events.

The microfluidic device includes a PDMS microfluidic channel formed in a base. An upper section covers the PDMS microfluidic channel. A gate, a source, and a drain are located in the PDMS microfluidic channel. A lipid bilayer-carbon nanotube transistor is connected to the gate, source, and drain by connectors.

Additional lipid bilayer-carbon nanotube transistors can be included in the system to provide an array of nanotube transistors. For example, the system also includes a lipid bilayer-carbon nanotube transistor. The lipid bilayer-carbon nanotube transistor is connected to the gate, a source, and a drain by connectors.

The lipid bilayer-carbon nanotube transistor comprises a single-wall carbon nanotube, a hydrophilic cushion, and a lipid bilayer. The single-wall carbon nanotube is shielded with the lipid bilayer. The hydrophilic cushion is located between the single-wall carbon nanotube and the lipid bilayer.

The lipid bilayer-carbon nanotube transistor includes ion channels. The ion channels are connected to the lipid bilayer and the lipid bilayer serves as a matrix for the ion channels. The nanotube generates the sensor readout and the lipid bilayer provides the selectivity to the analyte.

The single-wall carbon nanotube is surrounded by the hydrophilic cushion and the lipid bilayer. The ion channel is connected to the lipid bilayer. The lipid bilayer serves as a matrix for the ion channel.

The structural details of the microfluidic device having been described the operation of the microfluidic device will now be considered. The lipid bilayer-carbon nanotube transistor is suspended between source electrode and drain electrode. The gate electrode is on the bottom of the channel. The whole device is covered with a PDMS mold with microfluidic channels.

The lipid bilayer-carbon nanotube transistor provides a nanoscale biosensor for detection of pore-forming biological toxins. The lipid bilayer-carbon nanotube transistor incorporates the individual carbon nanotube surrounded by the lipid bilayer. The lipid bilayer serves as a highly-selective membrane controlling access to the nanotube surface. Toxins disrupt the bilayer's shielding ability and changes the nanotube's conductance. The lipid bilayer serves as a tunable semi-permeable membrane controlling the access to the nanotube, and the nanotube conductance provides a readout mechanism.

The main sensing element of the system is the carbon nanotube field-effect transistor (FET) with a single-wall carbon nanotube connecting the source. 105 and drain electrodes. The carbon nanotube is wrapped in a lipid bilayer shell that houses the sensing ion channel proteins. The bilayer also insulates the nanotube surface from the solution providing a barrier to non-specific interactions. The lipid bilayer does not contact the nanotube directly; instead, it rests on a thin permeable polymer cushion adsorbed on the nanotube.

The microfluidic device will detect the presence of pore-forming bacterial toxins, since many toxins attack cells by incorporating into the membrane and forming a channel through which the other components can either enter the cell or leak out of the cell. When the microfluidic device is exposed to a solution of a redox species in the absence of the toxin, the lipid bilayer blocks the access to the nanotubes. When the toxin incorporates into the bilayer and opens up a pore, the redox species are able to penetrate and bind to the nanotube surface, changing the nanotube's conductance and triggering the sensor readout.

The sensing principle exploits the high sensitivity of carbon nanotube transistors to gating by the external electric fields. Current flow through the ion channel in the lipid shell modulates the electric field in the vicinity of the nanotube and produces a large modulation of the transistor current. Alterations of the transport through the ion channel change transistor current, which is recorded by an external circuit. The device is also able to detect transport events through a single channel with a signal/noise ratio of more than. This high efficiency is a direct consequence of two the following two advantages: (a) large gain achieved with the transistor configuration and (b) direct electrical interfacing of biological ion channels to a reporting nanostructure.

The system provides a biosensor that can detect variations in ion transport through a protein pore using the lipid bilayer-carbon nanotube transistor. The system provides superior detection efficiency by using signal amplification, and also permits straightforward integration and multiplexing. The system 100 also provides a large amount of flexibility allowing seamless integration with different types of membrane-based sensing agents. The microfluidic device features high selectivity, low cost and low power consumption, and can serve as a wearable "bio-smoke alarm."

The microfluidic device can be briefly described as a carbon nanotube encapsulated by a lipid bilayer resting on a hydrophilic "cushion" layer. The bilayer supports the sensing ion channels and also acts as an "insulating jacket" to shield the nanotube from the solution species. This insulated carbon nanotube "wire" is suspended between microfabricated source and drain metal electrodes, forming a channel region of a field-effect transistor. The nanotube is suspended across a microfluidic channel with the third "gate" electrode running on the bottom of the channel.

Formation of a lipid bilayer around a naked carbon nanotube presents challenges. First, typical diameters of single-wall carbon nanotubes range from 1-2 nm, which is below a critical curvature of a common phospholipids bilayer. Second, the hydrophobic nanotube surface promotes the formation of a monolayer, not the bilayer that is necessary for membrane channel support. To remedy these problems, Applicants placed a semi-permeable hydrophilic polymer "cushion" layer between the nanotube and the bilayer. This layer is important for a number of reasons. First, the polymer provides hydrophilic support surface for the bilayer. Second, the additional polymer layer between the nanotube and the bilayer increases the size of the structure and helps to match the size of the support to the critical bilayer curvature. Third, interactions of the lipid headgroups with the polymer "cushion" stabilize the bilayer and increase its robustness. Fourth, the polymer "cushion," which typically contains up to 50% water, lifts the membrane from the substrate and helps to maintain natural environment for inserted protein channels, which may protrude past the bilayer.

Figure 5:
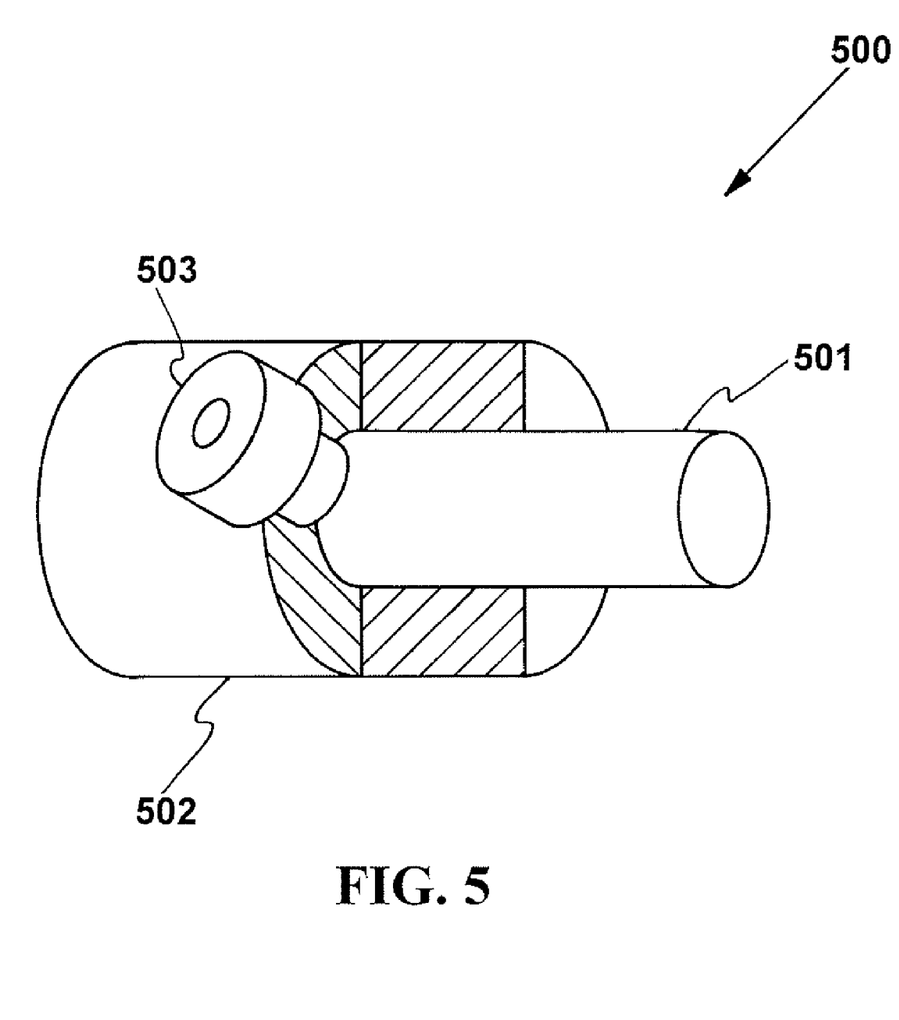
FIG. 5 illustrates another embodiment of a lipid bilayer on a nano-template constructed in accordance with the present invention.

Referring now to FIG. 5, another embodiment of a lipid bilayer on a nano-template constructed in accordance with the present invention is illustrated. The lipid bilayer on a nano-template is designated generally by the reference numeral 500. The lipid bilayer on a nano-template 500 can be briefly described as a nanotemplate 501 encapsulated by a lipid bilayer 502.

The specific lipid bilayer on a nano-template 500 shown in FIG. 5 is a lipid bilayer structure 502 around an inorganic nanowire 501. It is to be understood that other embodiments include other forms of nano-templates 501 and lipid bilayers 502. For example, the lipid bilayer 502 can be a one-dimensional (1-D) lipid bilayer 502. In one embodiment, a protein pore 503 is located in the lipid bilayer structure 502.

The structure of the lipid bilayer on a nano-template 500 having been described, the fabrication of the lipid bilayer on a nano-template will now be considered. First, an inorganic nanowire 501 is provided. Next a lipid bilayer is formed around the inorganic nanowire 501. In one embodiment, a protein pore 503 is formed in the lipid bilayer 502. The fabrication of the lipid bilayer on a nano-template utilizes the fabrication methods described above.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A lipid bilayer on a nano-template, comprising:
a nanotube or nanowire,
a lipid bilayer around said nanotube or nanowire,
a polymer cushion between said nanotube or nanowire and said lipid bilayer, and
a pore in said lipid bilayer.

2. The lipid bilayer on a nano-template of claim 1 wherein said polymer cushion comprises alternating polymer layers around said nanotube or nanowire and including a pore in said lipid bilayer.

3. The lipid bilayer on a nano-template of claim 1 wherein said polymer cushion comprises at least two alternating polymer layers around said nanotube or nanowire and including a pore in said at least two alternating polymer layers.

4. The lipid bilayer on a nano-template of claim 1 wherein said nanotube or nanowire is a single-wall nanotube.

5. The lipid bilayer on a nano-template of claim 1 wherein said nanotube or nanowire is a single-wall carbon nanotube.

6. The lipid bilayer on a nano-template of claim 1 wherein said nanotube or nanowire is a multi-wall nanotube.

7. The lipid bilayer on a nano-template of claim 1 wherein said nanotube or nanowire is a nanowire.

8. The lipid bilayer on a nano-template of claim 1 wherein said nanotube or nanowire is an inorganic nanowire.

9. The lipid bilayer on a nano-template of claim 1 including protein incorporated in said lipid bilayer and a protein pore in said protein incorporated in said lipid bilayer.

10. The lipid bilayer on a nano-template of claim 9 wherein said protein pore in said lipid bilayer is a protein pore that is sensitive to biowarfare agents.

11. The lipid bilayer on a nano-template of claim 9 wherein said protein pore in said lipid bilayer is an oligomeric protein pore in said lipid bilayer.

12. The lipid bilayer on a nano-template of claim 9 wherein said protein pore in said lipid bilayer is a protein pore that is sensitive to specific agents.

13. The lipid bilayer on a nano-template of claim 9 wherein said protein pore in said lipid bilayer is a protein pore that is sensitive to a full spectrum of biowarfare agents including bacteria, viruses and toxins.

14. The lipid bilayer on a nano-template of claim 9 wherein said protein pore in said lipid bilayer is a protein pore that is sensitive to a full spectrum of health related agents including bacteria, viruses and toxins.

15. A one-dimensional lipid bilayer on a nanotube template, comprising:
a nanotube,
a lipid bilayer around said nanotube,
a polymer cushion between said nanotube and said lipid bilayer, and
a protein pore in said lipid bilayer.

16. The one-dimensional lipid bilayer on a nanotube template of claim 15 wherein said polymer cushion comprises at least two alternating polymer layers around said nanotube.

17. The one-dimensional lipid bilayer on a nanotube template of claim 15 wherein said nanotube is a single-wall nanotube.

18. The one-dimensional lipid bilayer on a nanotube template of claim 15 wherein said nanotube is a single-wall carbon nanotube.

19. The one-dimensional lipid bilayer on a nanotube template of claim 15 wherein said nanotube is a multi-wall nanotube.

20. The one-dimensional lipid bilayer on a nanotube template of claim 15 wherein said nanotube is a multi-wall carbon nanotube.

21. The one-dimensional lipid bilayer on a nanotube template of claim 15 including protein incorporated in said lipid bilayer.

22. The one-dimensional lipid bilayer on a nanotube template of claim 15 wherein said protein pore in said lipid bilayer is a protein pore that is sensitive to biowarfare agents.

23. The one-dimensional lipid bilayer on a nanotube template of claim 15 wherein said protein pore in said lipid bilayer is an oligomeric protein pore in said lipid bilayer.

* * * * *

UNITED STATES PATENT AND TRADEMARK OFFICE
CERTIFICATE OF CORRECTION

PATENT NO. : 7,569,850 B2
APPLICATION NO. : 11/338513
DATED : August 4, 2009
INVENTOR(S) : Aleksandr Noy et al.

It is certified that error appears in the above-identified patent and that said Letters Patent is hereby corrected as shown below:

Title page, item (75) Inventors: change "Pieter Stoeve" to --Pieter Stroeve--.

Title page, item (73) Assignee: change "Lawrence Livermore National Security, LLC, Livermore, CA (US)" to --Lawrence Livermore National Security, LLC, Livermore, CA (US) and The Regents of the University of California, Oakland, CA (US)--.

Signed and Sealed this
Twenty-sixth Day of July, 2011

David J. Kappos
*Director of the United States Patent and Trademark Office*